United States Patent
Dzwonkiewicz

[19]

[11] Patent Number: 5,807,312
[45] Date of Patent: Sep. 15, 1998

[54] BOLUS PUMP APPARATUS

[76] Inventor: Mark R. Dzwonkiewicz, 578 Somerset #3, Crystal Lake, Ill. 60014

[21] Appl. No.: 862,569

[22] Filed: May 23, 1997

Related U.S. Application Data

[63] Continuation-in-part of Ser. No. 620,078, Mar. 21, 1996.

[51] Int. Cl.⁶ .................................................. A61M 1/00
[52] U.S. Cl. ................................ 604/30; 604/32; 604/248
[58] Field of Search .................................. 604/30, 32, 33, 604/34, 35, 131, 151, 246, 247, 248

[56] References Cited

U.S. PATENT DOCUMENTS

| | | | |
|---|---|---|---|
| 4,525,156 | 6/1985 | Benusa et al. | 604/32 X |
| 4,608,996 | 9/1986 | Brown | 604/32 X |
| 4,648,668 | 3/1987 | Hardwicki et al. | 604/32 |
| 4,832,685 | 5/1989 | Haines | 604/30 |
| 5,002,528 | 3/1991 | Palestrant | 604/30 X |
| 5,074,334 | 12/1991 | Onodera | 604/32 X |
| 5,340,364 | 8/1994 | Ghelli et al. | 604/32 |
| 5,352,214 | 10/1994 | Oscarsson | 604/32 X |
| 5,356,375 | 10/1994 | Higley | 604/30 |
| 5,443,453 | 8/1995 | Walker et al. | 604/32 X |
| 5,466,228 | 11/1995 | Evans | 604/32 X |

Primary Examiner—John D. Yasko
Attorney, Agent, or Firm—Lee, Mann, Smith, McWilliams, Sweeney & Ohlson

[57] ABSTRACT

A bolus pump apparatus is provided for connecting an IV bag to an infusion set. The bolus pump apparatus includes a pump connector assembly and a syringe pump. The pump connector assembly includes one or more valves adapted to provide selective fluid communication between the IV bag, the syringe pump, and the infusion set. The syringe draws a bolus of fluid from the IV bag through the pump connector assembly while the pump connector assembly prevents fluid within the infusion set from being drawn into the syringe. The syringe pumps a bolus of fluid from the syringe through the pump connector assembly to the infusion set, while the pump connector assembly prevents fluid within the syringe from being pumped into the IV bag.

20 Claims, 4 Drawing Sheets

FIG. 4

BOLUS PUMP APPARATUS

RELATED APPLICATIONS

This application is a continuation-in-part of application Ser. No. 08/620,078, filed Mar. 21, 1996, now pending.

BACKGROUND OF THE INVENTION

The present invention is directed to a bolus pump apparatus for withdrawing a quantity of fluid from a fluid container and pumping the fluid through an infusion set having a spike connector and a fluid dispensing tube to a patient, and in particular to a bolus pump apparatus having a pump mechanism and a connector assembly which connects the pump mechanism in selective fluid communication with the fluid container and the fluid dispensing tube of the infusion set.

At times it is desirable to inject a bolus, a quantity of fluid, into a patient during patient care. For example, during a cardiac arrest, liquid medication is often administered directly into the vein of a patient through an intravenous (IV) tube placed in the hand or midarm of the patient. Cardiac medications need to reach the patient's central circulation to be effective. Therefore, it is recommended to provide a fluid bolus through the IV tube after the administration of the cardiac medication to quickly move the cardiac medication to the heart. In the event a patient experiences a fluid volume loss, such as through trauma bleeding or internal bleeding, or experiences a drop in blood pressure, it is also recommended to quickly provide the patient fluid boluses. In children IV boluses are recommended to be given in 20 cc/kg doses. It has generally been recommended to use a syringe in providing a fluid bolus so that a large measured volume of fluid can be quickly injected under pressure into the patient.

There are presently several methods used to provide a fluid bolus after the administration of an intravenous medication. One method is to allow unrestricted flow of fluid from the IV bag to the patient through an infusion set. This not a true bolus of fluid, but is rather an IV flush of fluid. A second method requires medical personnel to take a syringe with a needle, clean a needle port on the IV bag, insert the needle through the IV bag port, draw out the desired quantity fluid from the IV bag into the syringe, clean an injection port in the IV tubing of the infusion set, insert the needle through the injection port of the IV tubing, pinch close the IV tubing behind the port and then administer the bolus from the syringe. This method is time consuming and involves high factors of risk. First, the IV bag may be inadvertently punctured by the needle when drawing the fluid into the syringe. Second, if the needle touches anything that is not sterile during this method the needle is contaminated and the process must be restarted. Third, the handling of a syringe with a needle exposes medical personnel to potential needle sticks. It is also difficult and time consuming to thread a needle into the injection ports of the IV bag and of the IV tubing. This procedure is made even more difficult and more dangerous when it takes place in the back of a moving ambulance which may be rocking from side to side, bouncing up and down, and increasing and decreasing in speed.

A third method involves the use of a three-way stopcock and a syringe attached to the stopcock with an extension tube. The stopcock is connected by a threaded connection to the end of the IV infusion set which is then connected to an extension set. The extension set is then connected to a catheter that is inserted into the patient. This method requires the assembly of three separate pieces of equipment, involves a high risk of contamination when connecting the ends of the individual parts, and does not permit the use of a standard infusion set including a spike connector member, an IV line, and a cannula. This apparatus adds additional length to the IV tubing and is located close to the patient as opposed to close to the IV bag. When the stopcock is located close to the patient the stopcock can easily be caught on another object when other procedures are being performed, especially when used in the back of an ambulance, resulting in the catheter being inadvertently pulled out of the patient. This method involves several steps, including switching the three-way stopcock to a draw position, opening the fluid flow control clamp on the IV tube, drawing fluid into the syringe, switching the stopcock to the bolus position, bolusing the fluid into the patient, switching the stopcock back to the line flow position, and readjusting the fluid flow clamp. These steps become confusing when the stopcock includes indicia such as arrows that merely indicate the direction of flow that is permitted by the stopcock as opposed to indicia that indicates the function that the stopcock is set to provide.

In addition, a pressurized bag sleeve may be placed over the IV bag to pressurize the IV bag and increase the rate of flow of fluid from the IV bag. This method does not allow measured doses of fluid from the IV bag to be delivered. It is also difficult to determine the overall amount of fluid that has been administered as a pressurized IV bag changes the correlation between the fluid level in the IV bag and the measurement markings on the wall of the bag. The present invention overcomes the difficulties and hazards in providing a fluid bolus that are now found in the current methods of administering a fluid bolus.

SUMMARY OF THE INVENTION

The present invention is directed to a fluid bolus pump apparatus for selectively drawing a measured quantity of fluid from a fluid container, such as an IV bag, and pumping the bolus of fluid through an infusion set including a spike connector and a fluid dispensing tube, such as an IV tube, to a patient. The bolus pump apparatus includes a pump mechanism, such as a syringe, and a pump connector assembly adapted to connect the pump mechanism in selective fluid communication with the fluid container and the fluid dispensing tube of the infusion set.

In one embodiment the pump connector assembly includes a first connector member, such as an IV spike, which selectively connects the pump connector assembly in fluid communication with the fluid container. The first connector member includes a first fluid passage extending therethrough having a first end and a second end. The first end of the first fluid passage is adapted to provide fluid communication with the fluid container. A first one-way valve is connected to a first connector member. The first one-way valve includes a second fluid passage having a first end and a second end. The first end of the second fluid passage provides fluid communication with the second end of the first fluid passage. The first one-way valve is adapted to allow fluid flow through the second fluid passage in a first direction from the first end of the second fluid passage to the second end of the second fluid passage, and is adapted to prevent fluid flow through the second fluid passage in a second direction from the second end of the second fluid passage to the first end of the second fluid passage.

A first fluid conduit is connected to the first one-way valve. The first fluid conduit includes a third fluid passage having a first end and a second end. The first end of the third fluid passage provides fluid communication with the second fluid passage of the first one-way valve. The first fluid conduit includes a port in fluid communication with the third fluid passage. The port is adapted to provide fluid communication between the third fluid passage and the pump mechanism. The pump mechanism is attached to the first fluid conduit in fluid communication with the port and the third fluid passage of the first fluid conduit. A second one-way valve is connected to the first fluid conduit. The second one-way valve includes a fourth fluid passage having a first end and a second end. The first end of the fourth fluid passage provides fluid communication with the third fluid passage of the first conduit. The second one-way valve is adapted to allow fluid flow through the fourth fluid passage in a first direction from the first end of the fourth fluid passage to the second end of the fourth fluid passage, and is adapted to prevent fluid flow through the fourth fluid passage in a second direction from the second end of the fourth fluid passage to the first end of the fourth fluid passage.

A second fluid conduit is attached to the second one-way valve. The second fluid conduit includes a fifth fluid passage including a first end and a second end. The first end of the fifth fluid passage provides fluid communication with the fourth fluid passage of the second one-way valve. The fifth fluid passage provides fluid communication between the fourth fluid passage of the second valve and the fluid dispensing tube of the infusion set. A second connector member, such as a spike receiving member, selectively connects the second fluid conduit to the spike connector and the fluid dispensing tube of the infusion set such that the fifth fluid path is in fluid communication with the fluid dispensing tube. A fluid flow control mechanism such as an adjustable clamp is attached to the second fluid conduit to selectively control the flow rate of fluid through the fifth fluid passage.

The pump mechanism of the bolus pump apparatus withdraws fluid from the fluid container through the first one-way valve into the third fluid passage and the syringe, while the second one-way valve prevents fluid within the fluid dispensing tube and the fifth fluid passage from being drawn into the third fluid passage and the syringe. The pump mechanism administers the fluid bolus by pumping withdrawn fluid out of the syringe through the second one-way valve into the fluid dispensing tube, while the first one-way valve prevents fluid in the third fluid passage and syringe from flowing into the fluid container. The on-off action of the valves occurs only with syringe activation, otherwise fluid from the IV bag flows freely through both valves and the flow rate will be controlled by a roller clamp.

In another embodiment the pump connector assembly of the bolus pump apparatus includes a spike connector member including a first fluid passage that is adapted to be connected in fluid communication with the fluid container. The pump connector assembly includes a first conduit having a first end, a second end and a second fluid passage extending from the first end of the first conduit to the second end of the first conduit. The first end of the first conduit is connected to the spike connector member such that the first fluid passage is in fluid communication with the second fluid passage. The pump connector assembly includes a valve having a housing and a rotor that is selectively rotatable within the housing between a first flow position, a second draw position and a third bolus position. The rotor includes a third fluid passage. The second end of the first conduit is attached to the housing such that the second fluid passage is in selective fluid communication with the third fluid passage of the rotor. A second conduit having a first end connected to the housing of the valve and a second end includes a fourth fluid passage extending from the first end of the second conduit to the second end of the second conduit such that the fourth fluid passage is in selective fluid communication with the third fluid passage of the rotor. A third conduit having a first end attached to the housing and a second end includes a fifth fluid passage extending from the first end of the third conduit to the second end of the third conduit such that the fifth fluid passage is in selective fluid communication with the third fluid passage of the rotor. The second end of the third conduit is adapted to be connected to the pump mechanism to provide fluid communication between the fifth fluid passage and the pump mechanism. A spike-receiving connector member is connected to the second end of the second conduit in fluid communication with the fourth fluid passage. The spike-receiving connector member is adapted to receive the spike connector of the infusion set to provide fluid communication between the fourth fluid passage and the fluid dispensing tube of the infusion set.

When the rotor is rotated to the first flow position, the third fluid passage provides fluid communication between the second fluid passage and the fourth fluid passage such that the bolus pump apparatus allows fluid to flow by gravity from the fluid container to the infusion set and the patient. When the rotor is rotated to the second draw position, the third fluid passage provides fluid communication between the second fluid passage and the fifth fluid passage such that the bolus pump apparatus allows the pump mechanism to draw fluid from the fluid container while preventing fluid within the fluid dispensing tube of the infusion set from being drawn into the pump mechanism. When the rotor is rotated to the third bolus position, the third fluid passage provides fluid communication between the fifth fluid passage and the fourth fluid passage such that the bolus pump apparatus allows the pump mechanism to pump fluid into the fluid dispensing tube of the infusion set while preventing fluid from being pumped into the fluid container.

DETAILED DESCRIPTION OF THE PREFERRED EMBODIMENTS

Figures 1, 3:
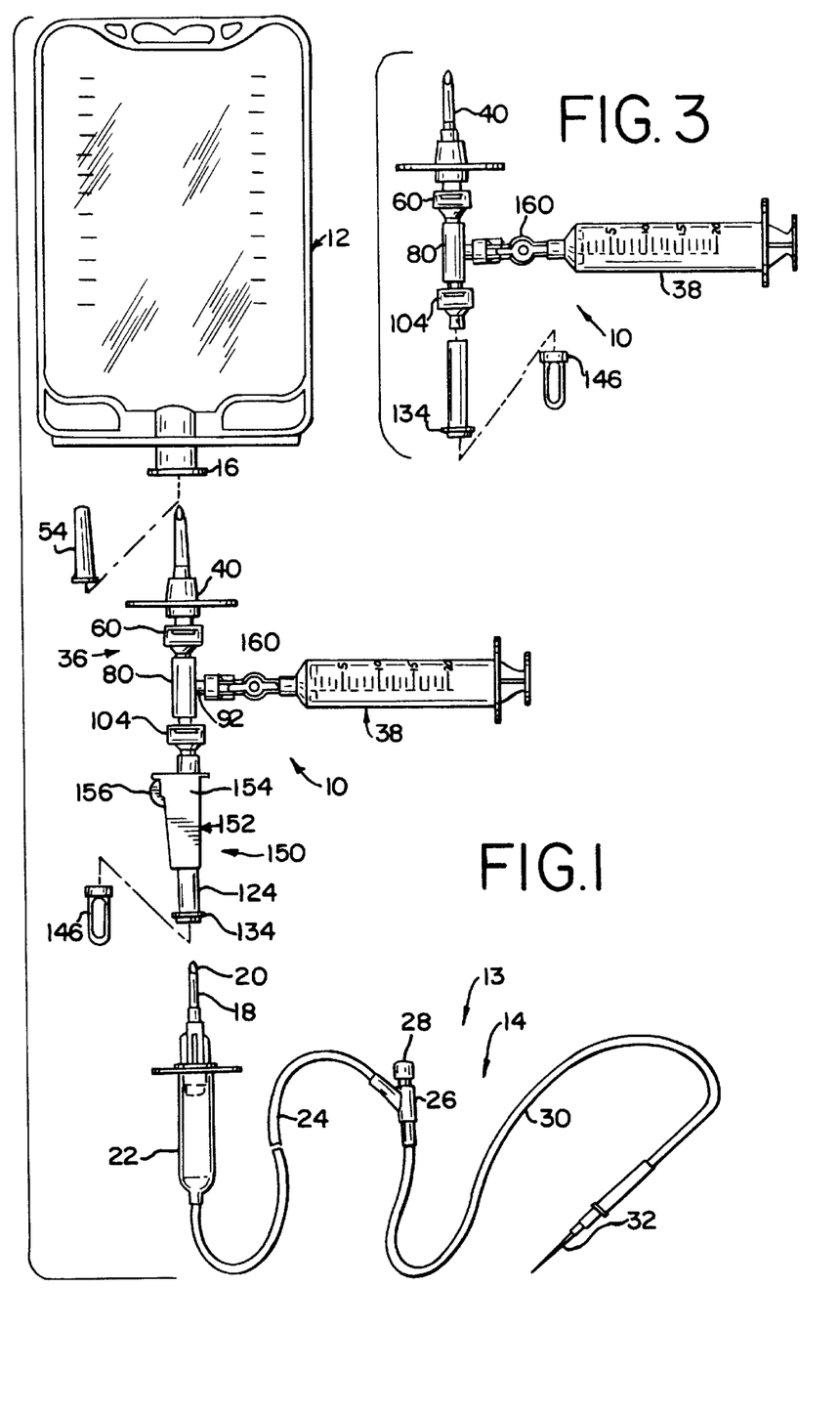
FIG. 1 shows a first embodiment of the bolus pump apparatus of the present invention in connection with a fluid container and an infusion set including a spike connector and a fluid dispensing tube.
FIG. 3 shows a second embodiment of the bolus pump apparatus of the present invention.

One embodiment of the bolus pump apparatus 10 of the present invention is shown in FIG. 1 in connection with a fluid dispensing container, such as an intravenous (IV) fluid bag 12, and an infusion set 13. While the fluid dispensing container is shown as being a bag, the fluid dispensing container may be a bottle, can or other types of containers which include a chamber for retaining and dispensing fluid such as a liquid medication. As used herein, a liquid medication is broadly considered to include any type of liquid which is used in the medical treatment of a patient, whether or not the liquid medication includes a drug. The IV bag 12 includes a spike receiving port 16 as is commonly found on IV bags currently in use. The port 16 provides selective access to the chamber of the IV bag 12. The infusion set 13 is also a standard item in current use. The infusion set 13 includes a fluid dispensing IV line 14, an IV spike connector 18, and a cannula 32 which is adapted to be inserted into a patient. The spike 18 includes a port 20 and a drip chamber 22 in fluid communication with the port 20. The fluid dispensing IV line 14 includes an IV tube 24 that connects a fitting 26 having a needle injection port 28 in fluid communication with the drip chamber 22, and an IV tube 30 that connects the fitting 26 in fluid communication with the cannula 32. A fluid path extends through the infusion set 13 from the port 20 of the spike 18, through the drip chamber 22 and the IV lines 24 and 30 to the cannula 32. The injection port 28 of the IV line 14 allows a fluid to be injected into the IV line 14 by insertion of a needle attached to a syringe through the port 28.

Figure 2:
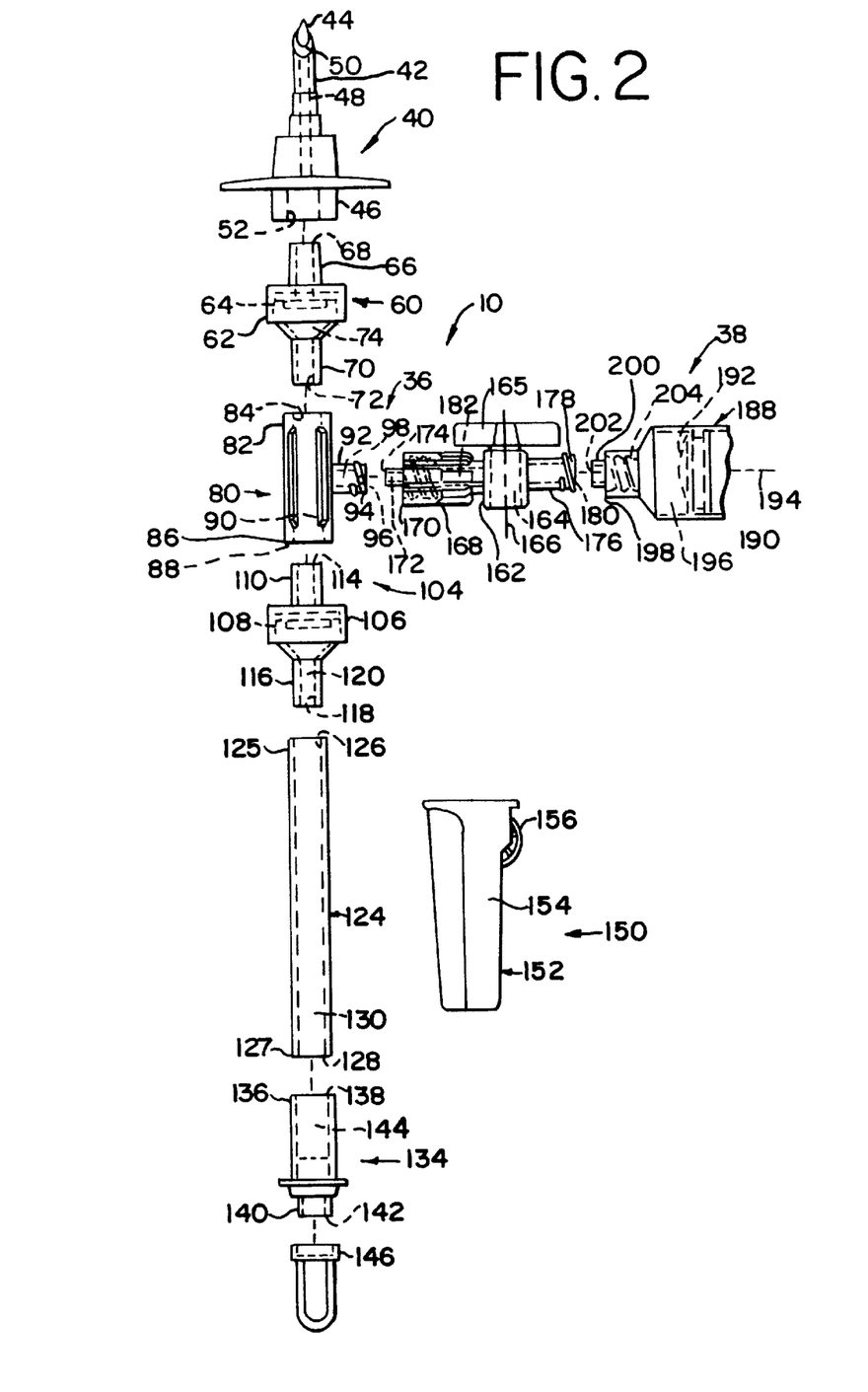
FIG. 2 is an exploded view of the bolus pump apparatus shown in FIG. 1.

The bolus pump apparatus 10 includes a pump connector assembly 36 and a pump mechanism 38. As best shown in FIG. 2, the pump connector assembly 36 includes a spike connector member 40. The spike connector member 40 includes a tubular shaft 42 having a pointed tip 44 and a base 46. The spike connector member 40 includes a first fluid passage 48 which extends within the shaft 42 from a port 50 in the tip 44 to a port 52 in the base 46. The shaft 42 of the spike connector member 40 is adapted to be inserted through the spike port 16 of the IV bag 12, such that the tip 44 punctures a membrane in the IV bag 12 and such that the port 50 and fluid passage 48 are in fluid communication with the chamber of the IV bag 12. The spike connector member 40 is thereby removably connected in fluid communication with the IV bag 12. A preferred spike connector member is a ten drop non-vented IV spike, Product No. 72036, as manufactured by Qosina Corp. of Edgewood, N.J. As best shown in FIG. 1, a removable cap 54 is provided to cover and maintain the sterility of the shaft 42 and fluid passage 48 of the spike connector member 40 until it is desired to connect the spike connector member 40 to the IV bag 12 whereupon the cap 54 is removed from the spike connector member 40.

The pump connector assembly 36 also includes a first one-way valve 60. The first one-way valve 60 includes a housing 62 having a chamber which contains a valve mechanism 64. A tubular stem 66 projects outwardly from the housing 62 and includes an inlet port 68 in the end of the stem 66. A tubular stem 70 projects outwardly from an opposite side of the housing 62 in generally coaxial alignment with the stem 66. The stem 70 includes an end having an outlet port 72. A second fluid passage 74 extends through the one-way valve 60 from the inlet port 68, through the stem 66, valve mechanism 64, housing 62 and stem 70 to the outlet port 72. The stem 66 is adapted to be inserted within the port 52 of the spike connector member 40 to thereby connect the first one-way valve 60 to the spike connector member 40 and provide fluid communication between the second fluid passage 74 and the first fluid passage 48. A preferred one-way valve is the CA-High-Flow check valve, Catalog No. R701, as manufactured by Resenex Corporation of Chatsworth, Calif. The valve mechanism 64 of the first one-way valve 60 automatically allows fluid flow through the second fluid passage 74 in a first direction from the inlet port 68 through the second fluid passage 74 to the outlet port 72. The valve mechanism 64 of the first one-way valve 60 also automatically prevents fluid flow through the second fluid passage 74 in a second direction, opposite to the first direction, from the outlet port 72 through the second fluid passage 74 to the inlet port 68.

Other types of valves, such as stopcock or on-off valves, may be used in place of the one-way valve 60. Such stopcock types of valves typically either allow fluid flow through the valve in either a first direction or a second and opposite direction, or prevent fluid flow in both directions. Thus with a stopcock type of valve, it would be necessary to adjust the valve between an open position when fluid flow through the valve is desired and a closed position when fluid flow through the valve is to be prevented. The selective opening and closing of a stopcock type of valve therefore requires extra time consuming steps which are avoided by the use of a one-way valve which automatically allows fluid flow in the first direction and automatically prevents fluid flow in the second direction.

The pump connector assembly 36 also includes a fluid conduit 80. The fluid conduit 80 is preferably a generally tubular T-shaped member. A preferred fluid conduit 80 is a T-connector with female luer adapter, Product No. 84048, as manufactured by Qosina Corp. of Edgewood, N.Y. The fluid conduit 80 includes a first end 82 having an inlet port 84 and a second end 86 having an outlet port 88. A third fluid passage 90 extends through the fluid conduit 80 from the inlet port 84 to the outlet port 88. The fluid conduit 80 also includes a stem 92. The stem 92 includes a threaded end 94 having an inlet/outlet pump port 96. A fourth fluid passage 98 extends within the stem 92 of the conduit 80 between the port 96 and the third fluid passage 90. The port 96 is thereby in fluid communication with the inlet port 84 and the outlet port 88 of the fluid conduit 80. The stem 70 of the one-way valve 60 is inserted into the end 82 of the fluid conduit 80 and is attached thereto such that the third fluid passage 90 is in fluid communication with the second fluid passage 74.

The pump connector assembly 36 also includes a second one-way valve 104 which is constructed substantially identical to the first one-way valve 60. The second one-way valve 104 includes a housing 106 having a chamber which contains a valve mechanism 108. A tubular stem 110 projects outwardly from the housing 106 and includes an inlet port 114 in the end of the stem 110. A tubular stem 116 projects outwardly from an opposite side of the housing 106 in generally coaxial alignment with the stem 110. The stem 116 includes an end having an outlet port 118. A fifth fluid passage 120 extends through the second one-way valve 104 from the inlet port 114, through the stem 110, valve mechanism 108, housing 106 and stem 116 to the outlet port 118. The stem 110 is adapted to be inserted within the second end 86 of the fluid conduit 80 to thereby connect the second one-way valve 104 to the fluid conduit 80 and provide fluid communication between the fifth fluid passage 120 and the third fluid passage 90. A preferred one-way valve is the CA-High-Flow check valve, Catalog No. R701, as manufactured by Resenex Corporation of Chatsworth, Calif. The valve mechanism 108 of the second one-way valve 104 automatically allows fluid flow through the fifth fluid passage 120 in a first direction from the inlet port 114 through the fifth fluid passage 120 to the outlet port 114. The valve mechanism 108 of the second one-way valve 104 also automatically prevents fluid flow through the fifth fluid passage 120 in a second direction, opposite to the first direction, from the outlet port 118 through the fifth fluid passage 120 to the inlet port 114.

The pump connector assembly 36 may include a relatively short flexible and resilient fluid conduit tube 124. The fluid conduit 124 includes a first end 125 having an inlet port 126 and a second end 127 having an outlet port 128. A sixth fluid passage 130 extends through the fluid conduit 124 from the inlet port 126 to the outlet port 128. The fluid conduit 124 may be formed in various different lengths as desired. The stem 116 of the second one-way valve 104 is inserted into the first end 125 of the fluid conduit 124 such that the fluid conduit 124 is connected to the second one-way valve 104 with the sixth fluid passage 130 in fluid communication with the fifth fluid passage 120.

The pump connector assembly 36 also includes a spike-receiving connector member 134 which is adapted to receive and connect the IV spike 18 of the infusion set 13 in fluid communication with the sixth fluid passage 130. The connector member 134 includes a first end 136 having a port 138 and a second end 140 having a spike receiving port 142. A seventh fluid passage 144 extends between the port 138 and the port 142. The seventh fluid passage is closed by a membrane at the second end 140 which is adapted to be punctured by the IV spike 18. The second end 127 of the fluid conduit 124 is inserted into the first end 136 and is connected to the connector member 134 such that the sixth fluid passage 130 is in fluid communication with the seventh fluid passage 144. The spike receiving port 142 is adapted to receive the shaft of the IV spike 18 of the infusion set 13 such that the port 20 of the IV spike 18 is in fluid communication with the seventh fluid passage 144. A removable cap 146 covers the second end 140 and encloses the seventh fluid passage 144 to maintain sterility until the pump connector assembly 36 is to be used, whereupon the cap 146 is removed from the connector member 134.

The pump connector assembly 136 may also include a flow control mechanism 150, such as a roller clamp 152, which is operatively attached to the fluid conduit 124. The roller clamp 152 includes a housing 154 through which the fluid conduit 124 extends and a rotatable wheel 156. The wheel 156 is selectively movable between a first end of the housing 154 wherein the sixth fluid passage 130 of the fluid conduit 124 is unrestricted to provide a maximum rate of flow of fluid through the fluid conduit 124, and a second end of the housing 154 wherein the sixth fluid passage 130 of the fluid conduit 124 is completely restricted such that fluid flow through the sixth fluid passage 130 is prevented. The wheel 156 may be selectively positioned between the opposite ends of the housing 154 such that various different rates of fluid flow through the sixth fluid passage 130 can be provided as desired. One type of roller clamp 152 that is suitable for use is Product No. 14020 as manufactured by Qosina Corp. of Edgewood, N.Y. Other types of flow control mechanisms 150 may be used as desired.

As the IV line 14 of the infusion set 13 is often provided with a flow control mechanism, in such cases, the pump connector assembly 36 need not include a flow control mechanism 150, as shown in FIG. 3. However, it is preferable to provide the flow control mechanism 150 in conjunction with the pump connector assembly 36, such that it is located adjacent to the components of the bolus pump apparatus 10 and the IV bag 12, even if the IV line 14 includes a flow control mechanism. When the flow control mechanism is provided on the IV line 14, it can be located anywhere along the length of the IV line 14 and therefore can be difficult to locate when time is of the essence, whereas the flow control mechanism 150 is easily locatable. When a flow control mechanism 150 is not used in connection with the pump connector assembly 36, the fluid conduit 124 may also be eliminated, and the connector member 134 may be attached directly to the second one-way valve 104, such that the fluid passage 144 is in fluid communication with the fluid passage 120.

The pump connector assembly 36 may also include a valve 160. The valve 160 includes a housing 162 having a rotor 164 located therein. The rotor 164 includes an actuator member 165 and is selectively rotatable about an axis 166 between an open position and a closed position. The valve 160 includes a stem 168 having a tubular threaded end 170 which is adapted to receive and removably engage the threaded end 94 of the stem 92 of the fluid conduit 80. The stem 168 also includes a fluid conduit 172 concentrically located within the tubular threaded end 170 having an end with a port 174. The valve 160 also includes a second stem 176 having a threaded end 178 with a port 180. A fluid passage 182 selectively extends between the ports 174 and 180 through the rotor 164. The actuator member 165 selectively rotates the rotor 164 to a first open position wherein the rotor 164 allows fluid flow through the fluid passage 182 between the ports 174 and 180. The actuator member 165 also selectively rotates the rotor 164 to a second closed position wherein the rotor 164 prevents fluid flow through the fluid passage 182 in either direction between the ports 174 and 180. The fluid conduit 172 of the valve 160 is adapted to be inserted through the port 96 of the fluid conduit 80 such that the fluid passage 182 is in fluid communication with the fluid passage 98 and the fluid passage 90. A preferred valve is a one-way stopcock with luer lock, Product No. 99705, as manufactured by Qosina Corp. of Edgewood, N.Y.

The pump mechanism 38 of the bolus pump apparatus 10 comprises a syringe 188. The syringe 188 includes a housing 190 and a plunger 192 slidably located within the housing 190. Selective sliding movement of the plunger 192 along an axis 194 creates a chamber 196 within the housing 190 of various different sizes a desired. The housing 190 includes a tubular threaded end 198 which is adapted to removably engage the threaded end 178 of the valve 160, or if a valve 160 is not being used, to threadably engage the threaded end 94 of the stem 92 of the fluid conduit 80. The housing 190 also includes a conduit 200 having a port 202 and a fluid passage 204 which extends from the port 202 to the chamber 196. The conduit 200 is adapted to be inserted through the port 180 of the valve 160 to provide fluid communication between the chamber 196 and fluid passage 182. If the valve 160 is not being used in connection with the pump connector assembly 36, the conduit 200 is adapted to be inserted through the port 96 of the stem 92 such that the chamber 196 and fluid passage 204 are in fluid communication with the fourth fluid passage 98 and third fluid passage 90 of the fluid conduit 80. Various different types and sizes of syringes 188 may be used as desired. In addition, other types of pump mechanisms may be used such as electrically, mechanically or pneumatically operated pumps.

While the syringe 188 can be directly attached to the stem 92 of the fluid conduit 80, the syringe 188 is preferably connected to the stem 92 by the valve 160. The valve 160 allows the fluid passages 182 and 98 to be selectively closed such that the syringe 188 can be removed from the valve 160, and a different size syringe attached to the valve 160, while fluid can continue to flow through the fluid passage 90. If the syringe 188 is not attached to the valve 160, a removable cap (not shown) is removably attached to the end 178 of the valve to maintain sterility. If the syringe 188 and the valve 160 are not attached to the stem 92 of the pump connector assembly 36, the removable cap (not shown) is removably attached to the end 94 of the stem 92 to maintain sterility. A preferred cap is Product No. 65353 as manufactured by Qosina Corp. of Edgewood, N.Y.

In operation, the cap 146 is removed from the connector member 134 and the IV spike 18 of the infusion set 13 is inserted through the port 142 such that the IV line 14 is connected in fluid communication with the fluid passages of the pump connector assembly 36. The cap 54 is then removed from the spike connector member 40 and the shaft 42 is inserted through the spike port 16 of the IV bag 12 such that the spike member 40 is connected to the IV bag 12 and is in fluid communication with chamber of the IV bag 12. Fluid from the chamber of the IV bag 12 flows by gravity through the port 50, through the fluid passage 48 of the spike connector member 40, through the fluid passage 74 of the first one-way valve 60 from the inlet port 68 to the outlet port 72, through the fluid passage 90 of the fluid conduit 80 from the inlet port 84 to the outlet port 88, through the fluid passage 120 of the second one-way valve 104 from the inlet port 114 to the outlet port 118, to the fluid passage 130 of the fluid conduit 124. The flow control mechanism 150 is selectively adjusted to provide the desired rate of flow of fluid from the fluid passage 130, through the fluid passage 144 of the connector member 134, to the port 20 and drip chamber 22 of the infusion set 13. The flow control mechanism 150 can adjust the flow of fluid through the fluid conduit 24 from no flow to full flow and any desired intermediate flow rate.

When a second medication, other than the medication in the IV bag 12, is to be administered to the patient, the needle of a syringe containing the second medication is inserted through the injection port 28 of the IV line 14 and the second medication is injected into the IV tube 30. To quickly pump or bolus the second medication through the IV tube 30 to the patient, and to the desired location within the patient, the flow control mechanism 150 is adjusted to a full flow position and, with the rotor 164 of the valve 160 in the open position, the plunger 192 of the syringe 188 is withdrawn from the housing 190 such that fluid from the chamber of the IV bag 12 is drawn through the fluid passage 48, the fluid passage 74, the fluid passage 90, the fluid passage 98 of the stem 92, the fluid passage 182 of the valve 160, and the fluid passage 202 into the chamber 196 of the syringe 188. As the fluid is being withdrawn from the IV bag 12 into the chamber 196 of the syringe 188, fluid within the fluid passage 130 of the fluid conduit 124 and within the IV line 14 is prevented from flowing through the fluid passage 120 to the fluid passage 90 and the chamber 196 of the syringe 188 by the second one-way valve 104 which prevents fluid from flowing through the fluid passage 120 from the port 118 to the port 114.

When a desired measured amount of fluid from the IV bag 12 has been withdrawn into the chamber 196 of the syringe 188, as indicated by the markings on the syringe, the plunger 192 can be pressed inwardly into the housing 190 to force fluid out of the chamber 196. As the plunger 192 is inserted into the housing 190, fluid from the chamber 196 flows through the fluid conduit 204, through the fluid passage 182 of the valve 160, through the fluid passage 98 of the stem 92, through the fluid passage 90 of the fluid conduit 80, through the fluid passage 120 of the second one-way valve 104 from the inlet port 114 to the outlet port 118, through the fluid passage 130 of the fluid conduit 124, and through the fluid passage 144 of the connector member 134 to the fluid passages of the infusion set 13. As the fluid is being pumped from the chamber 196 of the syringe 188 through the fluid passage 90 of the fluid conduit 80, fluid within the fluid passage 90 is prevented from flowing through the fluid passage 74 to the fluid passage 48 of the spike connector member 40 and to the IV bag 12 by the first one-way valve 60 which prevents fluid from flowing through the second fluid passage 74 from the port 72 to the port 68.

The bolus pump apparatus 10 allows a bolus of fluid of a desired measured quantity, such as 20 cc, to be quickly withdrawn from the IV bag 12 and pumped through the IV line 14 of the infusion set 13 into the patient to move the second medication to its desired location or to quickly administer large measured dosages of the fluid in the IV bag 12 into the patient. The plunger 192 of the syringe 188 can be repetitively withdrawn and inserted in a consecutive manner to provide multiple boluses of fluid. Once the desired quantity of fluid has been bolused to the patient, the flow control mechanism 150 can be readjusted to provide the desired flow rate of fluid from the IV bag 12 through the fluid passage 130 of the fluid conduit 124 to the patient.

Figure 4:
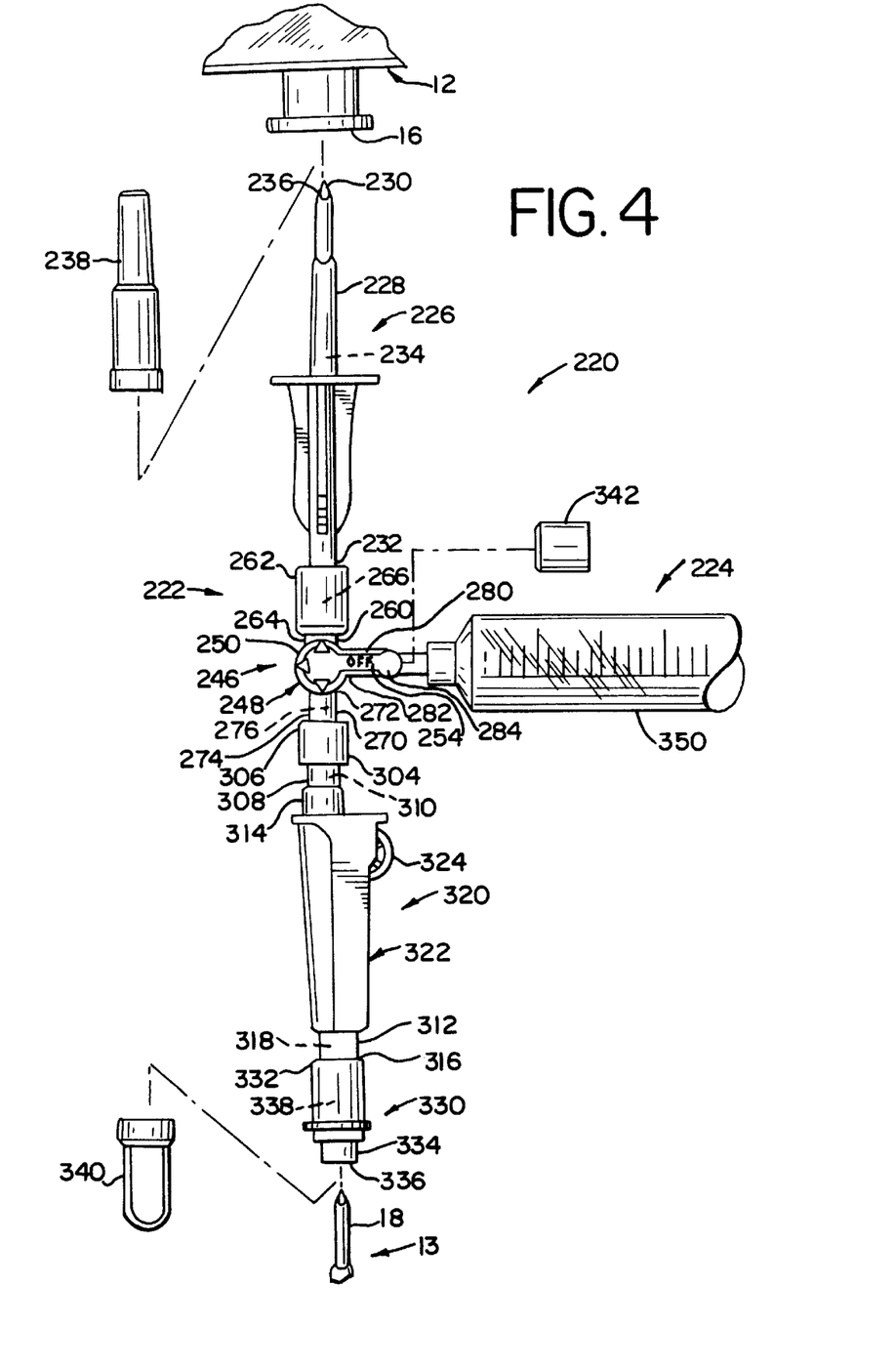
FIG. 4 shows a third embodiment of the bolus pump apparatus of the present invention.

Another embodiment of the bolus pump apparatus of the present invention is shown in FIG. 4 and is identified with the reference number 220. The bolus pump apparatus 220 includes a pump connector assembly 222 and a pump mechanism 224. The pump connector assembly 222 includes a spike connector member 226. The spike connector member 226 includes a tubular shaft 28 having a pointed tip 230 and a male threaded end 232. The spike connector member 226 includes a fluid passage 234 that extends within the shaft 228 from a port 236 in the tip 230 to a port in the base 232. The shaft 228 of the spike connector member 226 is adapted to be inserted through the spike-receiving port 16 of the IV bag 12 to place the fluid passage 234 in fluid communication with the chamber of the IV bag 12. The spike connector member 226 is thereby removably connected in fluid communication with the IV bag 12. A preferred spike connector member is a non-vented spike, Product No. 23210, as manufactured by Qosina Corp. of Edgewood, N.Y. A cap 238 is provided to cover and maintain the sterility of the shaft 228 and the fluid passage 234 of the spike connector member 226 until it is desired to connect to the spike connector member 226 to the IV bag 12 whereupon the cap 238 is removed from the spike connector member 226.

Figures 5A, 5B, 6A, 6B, 7A, 7B, 8:
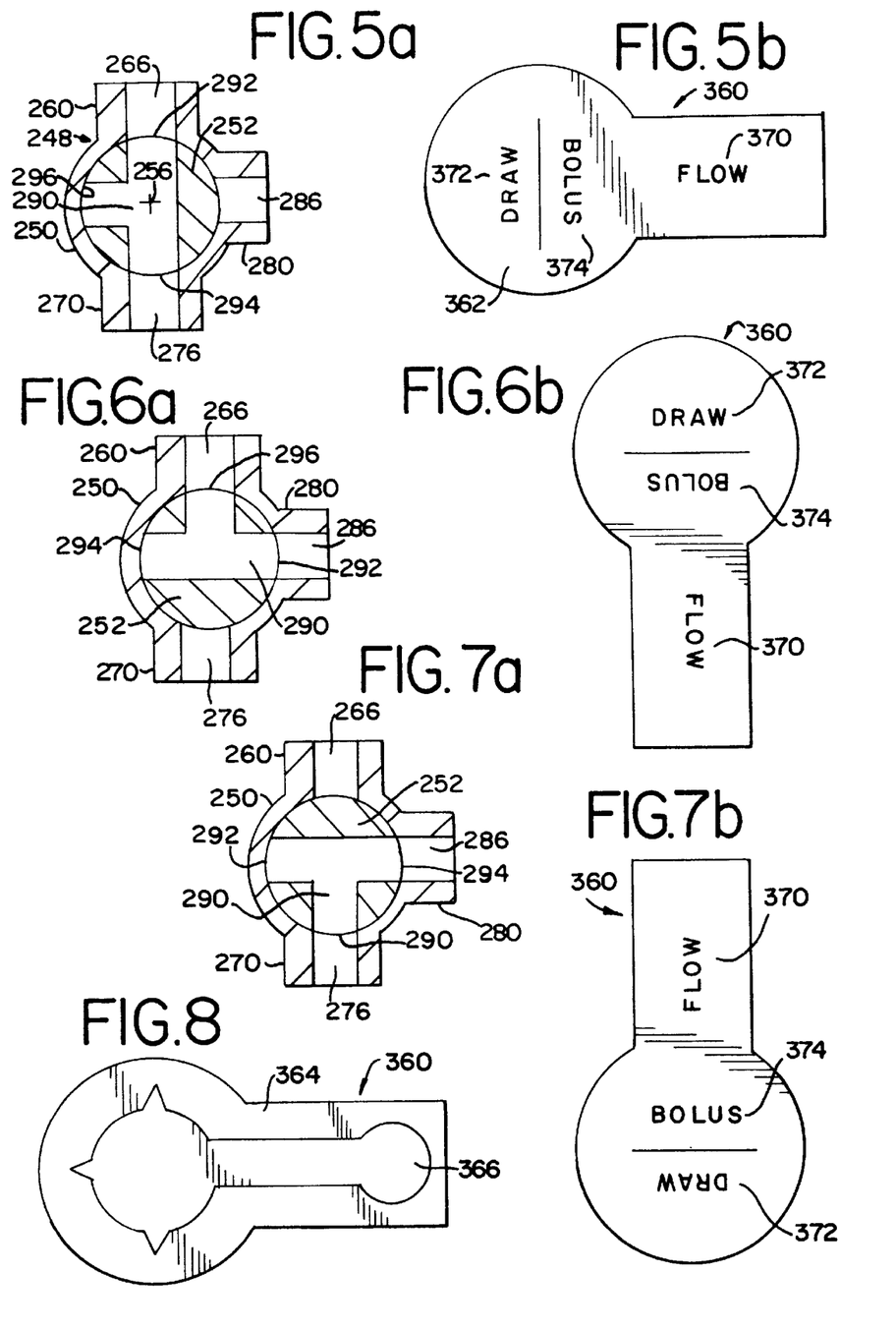
FIG. 5a is a cross-sectional view of the valve of the third embodiment of the bolus pump apparatus with the rotor of the valve shown in the flow position.
FIG. 5b is a front elevational view of the cap member that is attached to the actuator member of the rotor shown in the flow position.
FIG. 6a is a cross-sectional view of the valve of the third embodiment of the bolus pump apparatus with the rotor of the valve shown in the draw position.
FIG. 6b is a front elevational view of the cap member shown in the draw position.
FIG. 7a is a cross-sectional view of the valve of the third embodiment of the bolus pump apparatus with the rotor of the valve shown in the bolus position.
FIG. 7b is a front elevational view of the cap member shown in the bolus position.
FIG. 8 is a rear elevational view of the cap member.

The pump connector assembly 222 also includes a three-way stopcock 246. The stopcock 246 includes a three-way valve 248 having a housing 250 and a rotor 252 as best shown in FIG. 5a. An actuator member 254, such as a handle or knob is connected to the rotor 252. The rotor 252 is located within the housing 250 and is selectively rotatable within the housing 250 between a flow position, a draw position, and a bolus position by manual rotation of the actuator member 254 about an axis 256.

The stopcock 246 includes a first tubular conduit 260 having a first end 262 including a rotatable female threaded connector adapted to threadably receive and engage the male threaded end 232 of the spike connector member 226 and a second end 264 connected to the housing 250 of the valve 248. The first conduit 260 includes a fluid passage 266 that extends from the first end 262 to the second end 264 of the first conduit 260. The fluid passage 266 is in fluid communication with the fluid passage 234 of the spike connector member 226.

The stopcock 246 includes a second tubular conduit 270 having a first end 272 and a second end 274. The second end 274 preferably includes male threads. The second conduit 270 includes a fluid passage 276 that extends from the first end 272 to the second end 274. The first end 272 of the second conduit 270 is connected to the housing 250 of the valve 248.

The stopcock 246 includes a third tubular conduit 280 having a first end 282 that is connected to the housing 250 of the valve 248 and a second end 284. The third conduit 280 includes a fluid passage 286, as best shown in FIG. 5a, which extends from the first end 282 to the second end 284. The second end 284 preferably includes male threads.

The first conduit 260 and the second conduit 270 extend outwardly from opposite sides of the housing 250 generally diametrically away from one another and perpendicular to the axis 256. The third conduit 280 extends outwardly from the housing 250 transversely at a generally ninety degree angle relative to the first and second conduits 260 and 270, such that the conduits 260, 270 and 280 are arranged in a generally T-shaped arrangement.

As best shown in FIG. 5a, the rotor 252 of the valve 248 includes a fluid passage 290. The rotor 252 includes a first port 292, a second port 294 located generally diametrically across from the first port 292, and a third port 296 located at approximately ninety degrees or transversely to the first and second ports 292 and 294 relative to the axis 256. The ports 292, 294 and 296 are located relative to one another in a generally T-shaped arrangement. The fluid passage 290 extends between the first port 292, second port 294, and third port 296 such that the ports are in fluid communication with one another. The fluid passage 290 is formed in a generally T-shaped arrangement. A preferred three-way stopcock 246 is Product No. 99703, as manufactured by Qosina Corp. of Edgewood, N.Y. Each of the fluid passages 266, 276 and 286 are in selective fluid communication with the fluid passage 290.

The pump connector assembly 222 includes a connector member 304 having a female threaded first end 306 and a second end 308. The connector member 304 includes a fluid passage 310 extending from the first end 306 to the second end 308. The first end 306 of the connector member 304 is removably connected to the second end 274 of the second conduit 270 such that the fluid passage 310 is in fluid communication with the fluid passage 276. A preferred connector member 304 is a male luer, Product No. 71633-R, as manufactured by Qosina Corp. of Edgewood, N.Y.

The pump connector assembly 222 preferably includes a relatively short, flexible and resilient tube 312 having a first end 314 and a second end 316. The tube 312 includes a fluid passage 318 that extends from the first end 314 to the second end 316. The first end 314 is connected to the second end 308 of the connector member 304 such that the fluid passage 318 is in fluid communication with the fluid passage 310. A flow control mechanism 320, such as a roller clamp 322, is operatively attached to the tube 312. The roller clamp 322 includes a wheel 324 that may be selectively positioned to selectively restrict the fluid passage 318 to thereby control the rate of fluid flow through the fluid passage 318. The roller clamp 322 is constructed and operates similar to the roller clamp 152.

The pump connector assembly 222 includes a spike-receiving connector member 330 which is adapted to receive and connect the IV spike 18 of the infusion set 13 in fluid communication with the fluid passage 318 of the tube 312. The spike-receiving connector member 330 includes a first end 332 that is connected to the second end 316 of the tube 312 and a second end 334 including a spike-receiving port 336. A fluid passage 338 extends between the first end 332 and a second end 334. The fluid passage 338 is initially sealed closed by a membrane which is adapted to be punctured by the IV spike 18. The spike-receiving port 336 is adapted to receive the shaft of the IV spike 18 of the infusion set 13 such that the port 20 of the IV spike 18 is in fluid communication with the fluid passages 318 and 338.

A removable cap 340 covers the second end 334 and encloses the port 336 to maintain sterility until the pump connector assembly 226 is to be used, whereupon the cap 340 is removed from the spike-receiving connector member 330. A threaded cap 342 may be removably connected to the second end 284 of the third conduit 280 to close the fluid passage 286 and maintain sterility of the pump connector assembly 222. The cap 342 may be selectively removed from the third conduit 280 to allow the connection of the pump mechanism 224 to the third conduit 280.

The pump mechanism 224 of the bolus pump apparatus 220 comprises a syringe 350. The syringe 350 is constructed and operates in the same manner as the syringe 188. The syringe 350 is threadably engaged to the second end 284 of the third conduit 280 such that the syringe 350 is in fluid communication with the fluid passage 286. The syringe 350 may be removed from the third conduit 280 if desired and replaced by the cap 342.

The valve 248 of the pump connector assembly 222 may include an actuator cap 360 as shown in FIG. 5b attached to the actuator member 254. The actuator cap 360 includes a top surface 362 and a downwardly depending peripheral side wall 364. A recess 366 is formed within the side wall 364. The recess 366 is configured to matingly receive the actuator member 254 of the rotor 252 such that the actuator cap 360 and the actuator member 254 are conjointly rotatable with one another about the axis 256. The actuator cap 360 may be snap fit onto the actuator member 254 or attached thereto by an adhesive or other fastening means.

The actuator cap 360 includes first written visual indicia 370 comprising the word "FLOW" or other similar indicia such as the word "LINE", second written visual indicia 372 comprising the word "DRAW" or other similar indicia such as the word "SUCTION", and third written visual indicia 374 comprising the word "BOLUS" or other similar indicia such as the word "PUMP" on the top surface 362. When the cap 360 is positioned as shown in FIG. 5b, the first indicia 370 extends horizontally and is upright and readable from left to right. The second indicia 372 extends vertically in a non-readable position with the word extending from the bottom to the top of the indicia. The third indicia 374 extends vertically in a non-readable position such that the word extends from the top to the bottom of the indicia. Thus when the second indicia 372 is in a horizontal and upright readable position as shown in FIG. 6b, the third indicia 374 is in a horizontal, but inverted or upside down non-readable position.

In operation, the rotor 252 of the valve 248 is selectively rotatable between a first rotational flow position as shown in FIG. 5a, a second rotational draw position as shown in FIG. 6a, and a third rotational bolus position as shown in FIG. 7a. When the rotor 252 is located in the first rotational flow position as shown in FIG. 5a, the port 292 provides fluid communication between the fluid passage 266 and the fluid passage 290, and the port 294 provides fluid communication between the fluid passage 290 and the fluid passage 276, such that the fluid passage 290 provides fluid communication between the fluid passages 266 and 276 of the first and second conduits 260 and 270. The wall of the rotor 252 seals the passage 286 from the fluid passages 266, 276 and 290.

When the rotor 252 is in the flow position as shown in FIG. 5a, fluid from the IV bag 12 flows by gravity through the fluid passage 234 of the spike connector member 226, the fluid passage 266 of the first conduit, the fluid passage 290 of the rotor 252, the fluid passage 276 of the second conduit 270, the fluid passage 310 of the connector member 304, the fluid passage 318 of the tube 312 to the fluid passage of the spike 18 of the infusion set 13. The flow control mechanism 320 can be adjusted to selectively control the flow rate of fluid through the fluid passage 318 to the infusion set 13. When the rotor 252 is in the flow position as shown in FIG. 5a, the actuator cap 360 attached to the rotor 252 is located in the position as shown in FIG. 5b wherein the first written indicia 370 is horizontal and upright in normal reading position providing visual indication of the position of the rotor 252 and the function to presently be performed by the bolus pump apparatus 220, while the indicia 372 and 374 are in non-readable positions.

When it is desired to provide the patient with a bolus of fluid, the rotor 252 is manually rotated ninety degrees by the actuator member 254 from the flow position to the draw position as shown in FIG. 6a. When the rotor 252 is in the draw position the port 296 provides fluid communication between the fluid passage 266 and the fluid passage 290 and the port 292 provides fluid communication between the fluid passage 290 and the fluid passage 286 such that the fluid passage 290 provides fluid communication between the fluid passages 266 and 286. The wall of the rotor 252 closes the fluid passage 276 and seals it from the fluid passages 266, 286 and 290. When the rotor 252 is in the draw position as shown in FIG. 6a, the actuator cap 360 is located in the position as shown in FIG. 6b wherein the second visual indicia 372 is horizontal and upright in a normal reading position providing visual indication of the position of the rotor 252 and the function to be provided by the bolus pump apparatus 220, while the indicia 370 and 374 are in non-readable positions. When the rotor 252 is in the draw position as shown in FIG. 6a, the syringe 350 may draw fluid from the IV bag 12 through the fluid passages 266, 286 and 290 into the chamber of the syringe. However, the rotor 252 prevents fluid within the fluid passage 276 and within the infusion set 13 from being drawn into the syringe 350.

Once the desired measured quantity of fluid has been drawn into the syringe 350, the rotor 252 is manually rotated 180° by the actuator member 254 and the actuator cap 360 from the draw position to the bolus position as shown in FIG. 7a. When the rotor 254 is in the bolus position the port 294 provides fluid communication between the fluid passage 286 and the fluid passage 290 and the port 296 provides fluid communication between the passage 290 and the fluid passage 276 such that the fluid passage 290 communication between the fluid passage 286 and 276. The wall of the rotor 252 closes the fluid passage 266 and seals it from the fluid passages 276, 286 and 290. When the rotor 252 is in the bolus position as shown in FIG. 7a, the actuator cap 360 is located in the position as shown in FIG. 7b wherein the third indicia 374 is horizontal and upright in a normal reading position to indicate the rotational position of the rotor 252 and the function to be provided by the bolus pump apparatus 220, while the indicia 370 and 372 are in non-readable positions. When the rotor 252 is in the bolus position as shown in FIG. 7a, the syringe 350 is in fluid communication with the infusion set 13 such that fluid within the syringe 350 may be pumped through the fluid passages 286, 290 and 276 to the infusion set 13 and the patient. Thereafter the rotor 252 may be rotated to the flow position or to the draw position.

The bolus pump apparatus 220 places the roller clamp 152 in a close and fixed proximity to the stopcock 246, and places both the roller clamp 152 and the stopcock 246 in a close and fixed proximity to the IV bag 12, such that in use the stopcock 246 and the roller clamp 152 are always located in an out of the way position relative to the patient and in the same position relative to the IV bag 12. The stopcock 246 and the roller clamp 152 are therefore always easily locatable during use of the bolus pump apparatus 220 in the provision of IV fluids to a patient.

Various features of the invention have been particularly shown and described in connection with the illustrated embodiments of the invention, however, it must be understood that these particular arrangements merely illustrate, and that the invention is to be given its fullest interpretation within the terms of the appended claims.

What is claimed is:

1. A bolus pump apparatus adapted to connect a pump mechanism in fluid communication with a fluid container and an infusion set having a fluid dispensing tube with a spike connector, said bolus pump apparatus comprising:

a spike connector member for connecting said bolus pump apparatus to the fluid container, said spike connector member including a first fluid passage having a first end and a second end, said first end of said first fluid passage adapted to provide fluid communication with the fluid container;

a first valve connected to said spike connector member, said first valve including a second fluid passage having a first end and a second end, said first end of said second fluid passage providing fluid communication with said second end of said first fluid passage, said first valve adapted to allow fluid flow through said second fluid passage in a first direction from said first end of said second fluid passage to said second end of said fluid passage and adapted to prevent fluid flow through said second fluid passage in a second direction from said second end of said second fluid passage to said first end of said second fluid passage;

a first fluid conduit having a first end and a second end, said first end of said first fluid conduit connected to said first valve, said first fluid conduit including a third fluid passage having a first end and a second end, said first end of said third fluid passage providing fluid communication with said second fluid passage of said first valve, said first fluid conduit including a port in fluid communication with said third fluid passage between said first end and said second end of said third fluid passage, said port adapted to provide fluid communication between said third fluid passage and the pump mechanism;

a second valve connected to said second end of said first fluid conduit, said second valve including a fourth fluid passage having a first end and a second end, said first end of said fourth fluid passage providing fluid communication with said third fluid passage of said first fluid conduit, said second valve adapted to allow fluid flow through said fourth fluid passage in a first direction from said first end of said fourth fluid passage to said second end of said fourth fluid passage and adapted to prevent fluid flow through said fourth fluid passage in a second direction from said second end of said fourth fluid passage to said first end of said fourth fluid passage; and a spike-receiving connector member connected to said second valve in fluid communication with said second end of said fourth fluid passage of said second valve, said spike-receiving connector member adapted to receive the spike connector of the infusion set to provide fluid communication between said fourth fluid passage and the fluid dispensing tube;

whereby said bolus pump apparatus allows the pump mechanism to withdraw fluid from the fluid container through said first valve while said second valve prevents fluid within the fluid dispensing tube from being drawn into said third fluid passage, and allows the pump mechanism to pump fluid from said third fluid passage through said second valve into the fluid dispensing tube while said first valve prevents fluid in said third fluid passage from flowing into the fluid container.

2. The bolus pump apparatus of claim 1 including a third valve having a first end and a second end and a fifth fluid passage extending therethrough, said first end of said third valve being attached to said first fluid conduit such that said fifth fluid passage is in fluid communication with said port of said first fluid conduit, said third valve adapted to selectively open and close said fifth fluid passage, said second end of said third valve adapted to be connected to the pump mechanism.

3. The bolus pump apparatus of claim 1 including a second fluid conduit extending between said second valve and said spike-receiving connector member providing fluid communication between said fourth fluid passage of said second valve and said spike-receiving connector member.

4. The bolus pump apparatus of claim 3 including means for selectively controlling the flow rate of fluid through said second fluid conduit.

5. The bolus pump apparatus of claim 3 including a roller clamp for selectively controlling the flow rate of fluid through said second fluid conduit.

6. The bolus pump apparatus of claim 1 wherein said first and second valves each respectively comprise a one-way valve.

7. The bolus pump apparatus of claim 1 including a pump mechanism connected to said first fluid conduit in fluid communication with said port of said first fluid conduit.

8. The bolus pump apparatus of claim 7 wherein said pump mechanism comprises a syringe.

9. A bolus pump apparatus adapted to connect a pump mechanism in fluid communication with a fluid container and an infusion set including a fluid dispensing tube and a spike connector, said bolus pump apparatus comprising:

a spike connector member including a first fluid passage, said spike connector member adapted to be connected to the fluid container such that said first fluid passage is in fluid communication with the fluid container;

a first conduit having a first end and a second end and a second fluid passage extending from said first end of said first conduit to said second end of said first conduit, said first end of said first conduit being connected to said spike connector member such that said first fluid passage is in fluid communication with said second fluid passage;

a valve having a housing and a rotor that is selectively rotatable between a first position, a second position and a third position, said rotor including a third fluid passage, said second end of said first conduit being attached to said housing such that said second fluid passage is in selective fluid communication with said third fluid passage of said rotor;

a second conduit having a first end and second end and a fourth fluid passage extending from said first end of said second conduit to said second end of said second conduit, said first end of said second conduit being attached to said housing such that said fourth fluid passage is in selective fluid communication with said third fluid passage of said rotor;

a third conduit having a first end and a second end and a fifth fluid passage extending from said first end of said third conduit to said second end of said third conduit, said first end of said third fluid conduit being connected to said housing such that said fifth fluid passage is in selective fluid communication with said third fluid passage of said rotor, said second end of said third conduit adapted to be connected to the pump mechanism to provide fluid communication between said fifth fluid passage and the pump mechanism;

a spike-receiving connector member connected to said second end of said second conduit in fluid communication with said fourth fluid passage, said spike-receiving connector member adapted to receive the spike connector of the infusion set to provide fluid communication between said fourth fluid passage and the fluid dispensing tube of the infusion set;

whereby when said rotor is selectively rotated to said first position said third fluid passage provides fluid communication between said second fluid passage and said fourth fluid passage such that said bolus pump apparatus allows fluid to flow from the fluid container into the infusion set, when said rotor is selectively rotated to said second position said third fluid passage provides fluid communication between said second fluid passage and said fifth fluid passage such that said bolus pump apparatus allows the pump mechanism to draw fluid from the fluid container while preventing fluid within the fluid dispensing tube of the infusion set from being drawn into the pump mechanism, and when said rotor is selectively rotated to said third position said third fluid passage provides fluid communication between said fifth fluid passage and said fourth fluid passage such that said bolus pump apparatus allows the pump mechanism to pump fluid into the fluid dispensing tube of the infusion set while preventing fluid from being pumped into the fluid container.

10. The bolus pump apparatus of claim 9 wherein said rotor of said valve includes a first port, a second port and a third port, said third fluid passage providing fluid communication between said first, second and third ports.

11. The bolus pump apparatus of claim 9 including a fourth fluid conduit extending between said second end of said second fluid conduit and said spike-receiving connector member providing fluid communication between said fourth fluid passage and said spike-receiving connector member.

12. The bolus pump apparatus of claim 11 including means for selectively controlling the flow rate of fluid through said fourth fluid conduit.

13. The bolus pump apparatus of claim 11 including a clamp for selectively controlling the flow rate of fluid through said fourth fluid conduit.

14. The bolus pump apparatus of claim 9 including a pump mechanism connected to said third fluid conduit in fluid communication with said fifth fluid passage.

15. The bolus pump apparatus of claim 14 wherein said pump mechanism comprises a syringe.

16. The bolus pump apparatus of claim 9 including a cap member attached to said rotor.

17. The bolus pump apparatus of claim 16 wherein said valve includes an actuator member attached to said rotor for providing selective rotational movement of said rotor and said cap member includes a recess adapted to receive said actuator member, said actuator member being inserted into said recess of said cap member such that selective rotation of said cap member provides rotation of said actuator member and said rotor.

18. The bolus pump apparatus of claim 16 wherein said cap member includes first indicia visually indicating when said rotor is located in said first rotational position, second indicia visually indicating when said rotor is located in said second position, and third indicia visually indicating when said rotor is located in said third position.

19. The bolus pump apparatus of claim 18 wherein said first indicia comprises a first word indicative of said rotor being located in said first position, said second indicia comprises a second word indicative of said rotor being located in said second position, and said third indicia comprises a third word indicative of said rotor being located in said third position.

20. The bolus pump apparatus of claim 18 wherein said first indicia is indicative of the function provided by said bolus pump apparatus when said rotor is located in said first position, said second indicia is indicative of the function provided by said bolus pump apparatus when said rotor is located in said second position, and said third indicia is indicative of the function provided by said bolus pump apparatus when said rotor is located in said third position.

* * * * *